United States Patent [19]

Kanai

[11] Patent Number: 5,201,707

[45] Date of Patent: Apr. 13, 1993

[54] INTRA-AORTIC BALLOON PUMP APPARATUS

[75] Inventor: Naritoshi Kanai, Anjo, Japan

[73] Assignee: Aisin Seiki Kabushiki Kaisha, Kariya, Japan

[21] Appl. No.: 858,404

[22] Filed: Mar. 27, 1992

[30] Foreign Application Priority Data

Mar. 29, 1991 [JP] Japan .................................. 3-065989

[51] Int. Cl.$^5$ .............................................. A61M 29/00
[52] U.S. Cl. ...................................... 604/100; 604/247
[58] Field of Search ................. 604/96, 98, 99, 100, 604/101, 247; 606/191-194

[56] References Cited

U.S. PATENT DOCUMENTS

| | | | |
|---|---|---|---|
| 3,901,246 | 8/1975 | Wallace | 604/100 |
| 4,733,652 | 3/1988 | Kantrowitz et al. | |
| 4,790,821 | 12/1988 | Stines | 604/98 |
| 4,856,510 | 8/1989 | Kowalewski | 604/100 |

*Primary Examiner*—John D. Yasko
*Attorney, Agent, or Firm*—Sughrue, Mion, Zinn, Macpeak & Seas

[57] ABSTRACT

The present invention is directed to an ultra-aortic balloon pump apparatus which comprises a catheter, a balloon connected to the catheter, a negative pressure source for withdrawing a fluid from the catheter and applying a negative pressure to the balloon through the catheter, and a check valve which is disposed between the catheter and the negative pressure source. The check valve is adapted to allow the fluid flow therethrough from the catheter to the negative pressure source and prevent the fluid from flowing from the negative pressure source to the catheter. The check valve defines therein a pressure chamber communicated with the balloon through the catheter, and which is deformed when the negative pressure is applied to the pressure chamber.

6 Claims, 5 Drawing Sheets

INTRA-AORTIC BALLOON PUMP APPARATUS

BACKGROUND OF THE INVENTION

1. Field of the Invention

The present invention relates to an intra-aortic balloon pump apparatus, more particularly to an intra-aortic balloon pump apparatus that enables it to determine whether the inside of a balloon pump is maintained at a negative pressure.

2. Description of the Prior Art

Conventionally, an intra-aortic balloon pump apparatus is connected to its exclusive pressure source through its supply inlet for helium gas and adapted to inflate and deflate a balloon by means of helium gas. Such an intra-aortic balloon pump apparatus is inserted into the patient, either percutaneously or through an incision, and advanced until it lies within the thoracic aorta descendens. Then, the balloon is inflated and deflated in synchronous relationship with the pulsation of the heart so as to reduce the load on the left ventricle and increase the amount of coronary blood flow.

Since the apparatus is inserted into the patient's body with the balloon wrapped, the inside of the balloon has to be maintained at a negative pressure without causing the balloon to be inflated, so that a check valve and syringe have been utilized.

In the above-described conventional intra-aortic balloon pump apparatus, however, there is no way for determining whether the inside of the balloon is actually maintained at a negative pressure, even though it has been maintained at a negative pressure by a negative pressure source. If a cylindrical holder for holding the wrapped balloon is removed therefrom when the inside of the balloon has not been maintained at a negative pressure, the balloon is inflated, so that it may not be inserted into the patient's body.

SUMMARY OF THE INVENTION

Accordingly, it is an object of the present invention to provide an intra-aortic balloon pump apparatus that enables it to determine whether the inside of a balloon pump is maintained at a negative pressure.

In accomplishing the above and other objects, an intra-aortic balloon pump apparatus comprises a catheter, a balloon connected to the catheter, a negative pressure source for withdrawing a fluid from the catheter and applying a negative pressure to the balloon through the catheter, and check valve means which is disposed between the catheter and the negative pressure source. The check valve means is adapted to allow the fluid flow therethrough from the catheter to the negative pressure source and prevent the fluid from flowing from the negative pressure source to the catheter. The check valve means defines therein a pressure chamber which is communicated with the balloon through the catheter, and the check valve means is deformed when the negative pressure is applied to the pressure chamber.

Preferably, the check valve means comprises a connecting member which has a first passage defined therethrough, a valve base which has a second passage defined therethrough and a recess formed on one end surface thereof and communicated with the second passage to provide a valve seat, a valve member which is received in the recess and seated on the valve seat for allowing the fluid flow therethrough from the catheter to the negative pressure source and preventing the fluid from flowing from the negative pressure source to the catheter, a bridge member which is disposed between one end surface of the connecting member and the other end surface of the valve base for supporting the connecting member in spaced relationship with the valve base, and a membrane tube which is disposed between the connecting member and the valve base for defining therein the pressure chamber and enclosing therein the bridge member. The pressure chamber is communicated with the first and second passages, and the membrane tube is depressed inwardly when the negative pressure is applied to the pressure chamber.

BRIEF DESCRIPTION OF THE DRAWINGS

The above stated object and following description will become readily apparent with reference to the accompanying drawings in which.

DESCRIPTION OF THE PREFERRED EMBODIMENT

Figure 2:
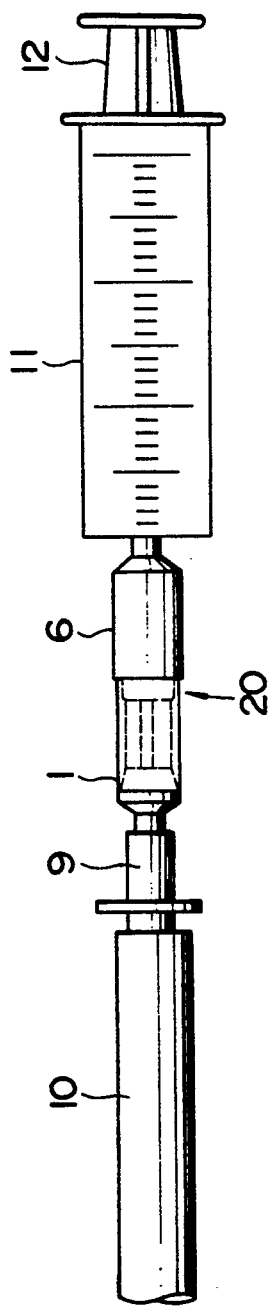
FIG. 2 is a side view illustrating a check valve and a syringe connected thereto in an embodiment of an intra-aortic balloon pump apparatus according to the present invention.
Figure 4:
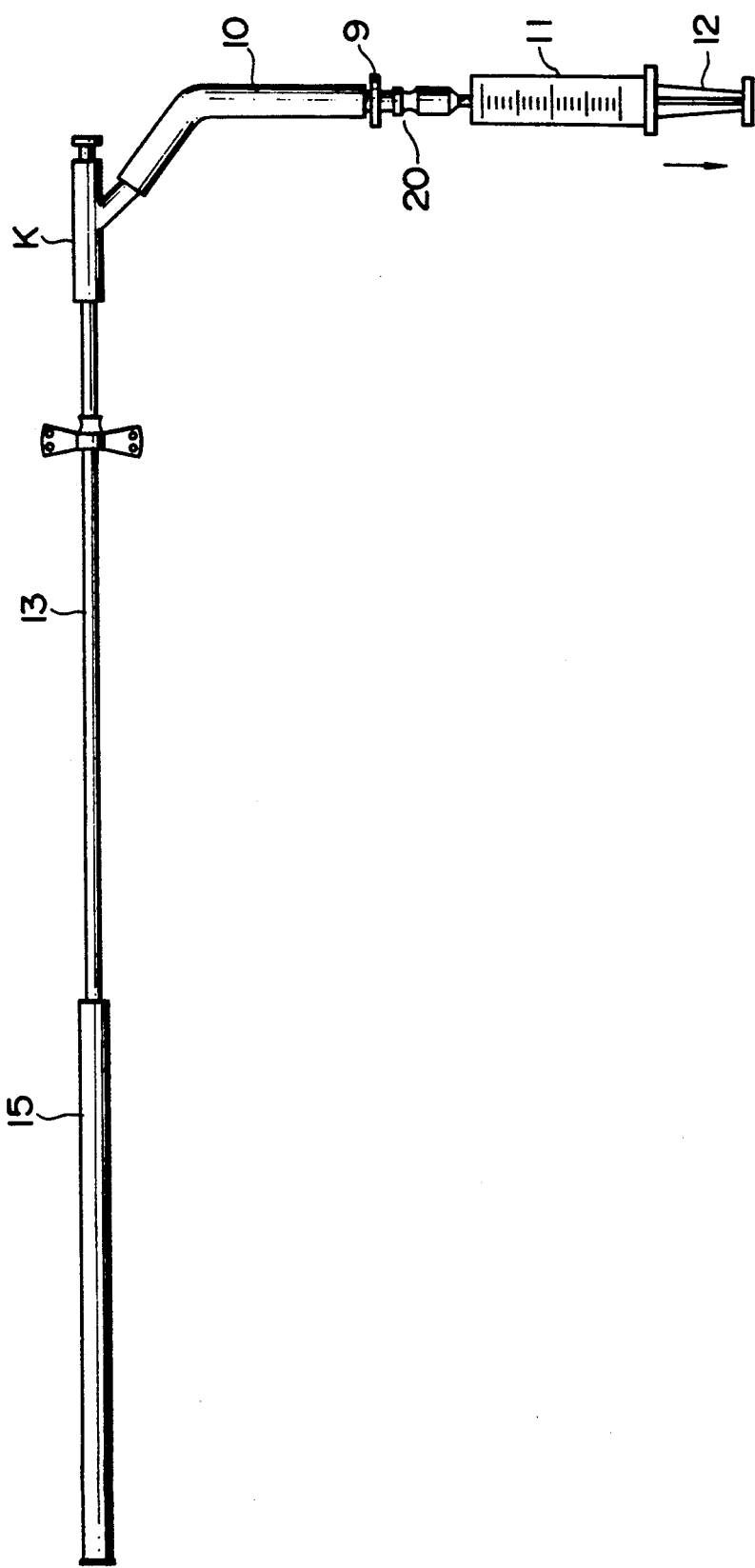
FIG. 4 is a side view of an embodiment of an intra-aortic balloon pump apparatus according to the present invention.

Referring to FIG. 2, there is illustrated a part of an embodiment including a cylindrical check valve 20 according to the present invention. The check valve 20 is connected at its cylindrical connecting member 1 to a connector 9 for connecting to a helium hose 10, which is communicated with a catheter 13 as shown in FIG. 4. The check valve 20 has a syringe receiving member 6 to which a syringe 11 having a piston 12 disposed therein is connected at its tip end.

Figure 5:
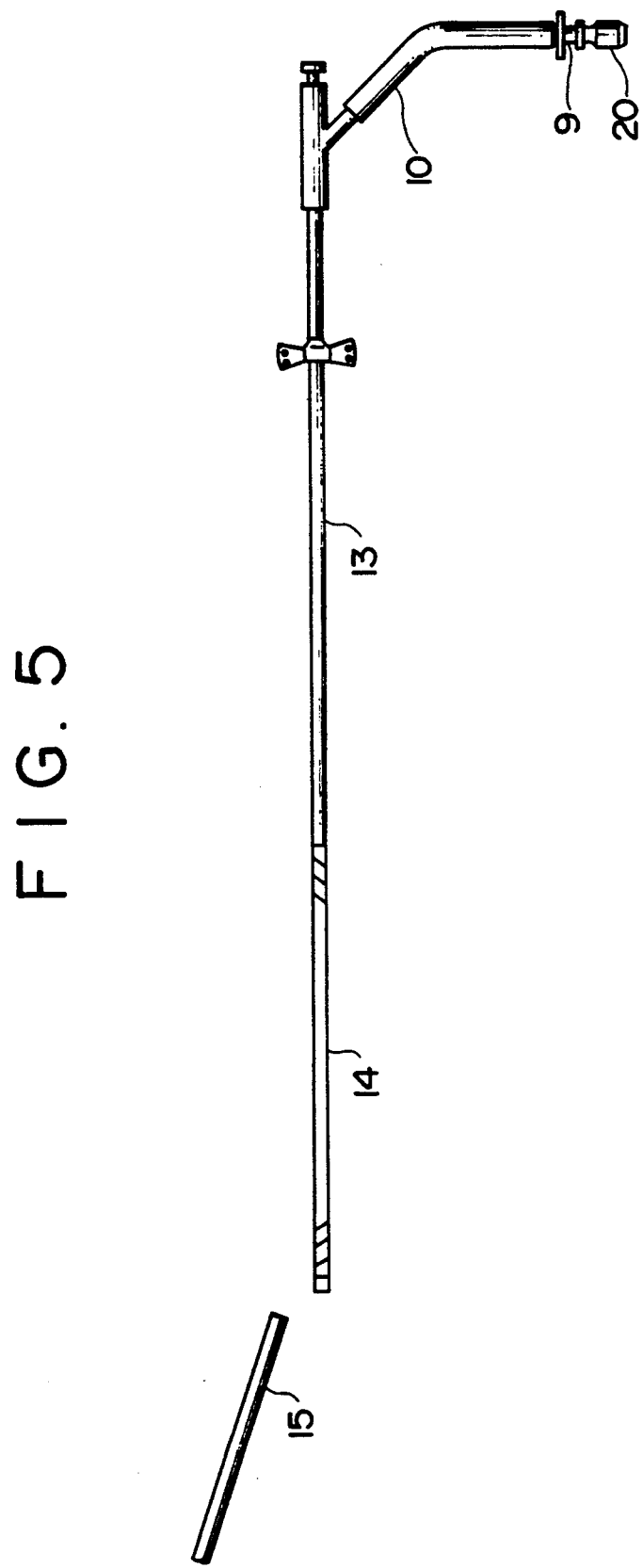
FIG. 5 is a side view of an intra-aortic balloon pump apparatus with a holder and syringe removed therefrom according to an embodiment of the present invention.

Referring to FIG. 4, the helium hose 10 is joined to a Y-shaped connector K which is connected to the catheter 13, and through which helium gas is introduced into the catheter 13. A balloon 14 shown in FIG. 5 is connected to the catheter 13 and wrapped therearound, while it is unwrapped from the catheter 13 after it has been inserted into the aorta and reached a predetermined position therein as described later. A cylindrical holder 15 is provided for enclosing the balloon 14 therein to hold it.

Figure 1:
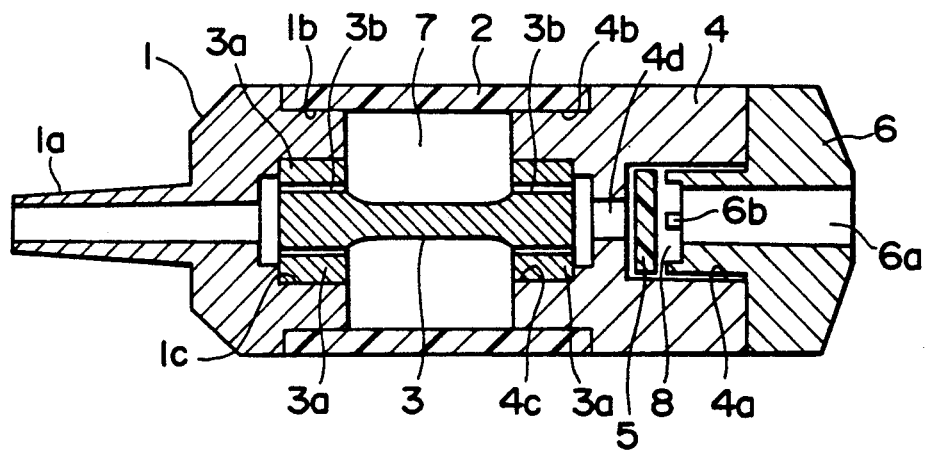
FIG. 1 is a sectional side view of a check valve used in an embodiment of an intra-aortic balloon pump apparatus according to the present invention.

FIG. 1 shows an enlarged sectional view of the check valve 20 which includes the connecting member 1 and a cylindrical valve base 4 arranged in spaced relationship therewith. The connecting member 1 is formed with a tubular portion 1a. Around peripheries of the connecting member 1 and valve base 4, stepped portions 1b and 4b are formed, respectively. Recesses 1c and 4c are formed respectively on the surfaces of the connecting member 1 and valve base 4 facing each other in the axial direction thereof. Fitted into these recesses 1c and 4c is a bridge member 3 having flange portions 3a, 3a at its both ends with small holes 3b, 3b defined axially therethrough.

Between the connecting member 1 and valve base 4, there is disposed a negative pressure indicating membrane 2 made of a thin elastic tube, silicone rubber tube for example, with the thickness of approximately 1 mm, which is adhered and fixed around the stepped portions 1b and 4b. Consequently, a negative pressure chamber 7 is defined within the membrane 2 and around the bridge member 3.

The valve base 4 has a recess 4a formed on the surface thereof opposite to the recess 4c, for fitting thereinto a tip end portion of a syringe receiving member 6 to form a valve chamber 8 between the bottom of the recess 4a and the tip end of the syringe receiving member 6 which has a passage 6a defined on its axis. In the valve base 4, there is formed a through hole 4d for communicating the bottom of recess 4a with the bottom of recess 4c. A disk-like valve member 5 is disposed within the valve chamber 8 to be seated on the bottom of the recess 4a. Several pieces of contact pins 6b are provided around the periphery of tip end of the member 6 extending in the axial direction thereof so as to contact with the valve member 5 when the helium gas is withdrawn from the valve chamber 8 through the passage 6a of the member 6, that is, when the valve member 5 is forced to move rightward in FIG. 1.

Thus, when the piston 12 of the syringe 11 is drawn rightward in FIG. 1 so that the gas is withdrawn from the chamber 7 and space communicated therewith, the valve member 5 is forced to move in the same direction to contact with the contact pins 6b. When the piston 12 is drawn rightward further, the gas within the chamber 7 and the space communicated therewith is withdrawn and introduced into the syringe 11 through each gap between the contact pins 6b next to each other to provide a negative pressure state in the chamber 7 and the space communicated therewith. When the gas has been withdrawn from the chamber 7 and the space, and then the syringe 11 is removed from the syringe receiving member 6, atmospheric pressure is applied on the valve member 5. Therefore, the valve member 5 is forced to move leftward in FIG. 1 to close the through hole 4d. As a result, the chamber 7 of the check valve 20 and the space communicated therewith are maintained at the negative pressure.

Figure 3:
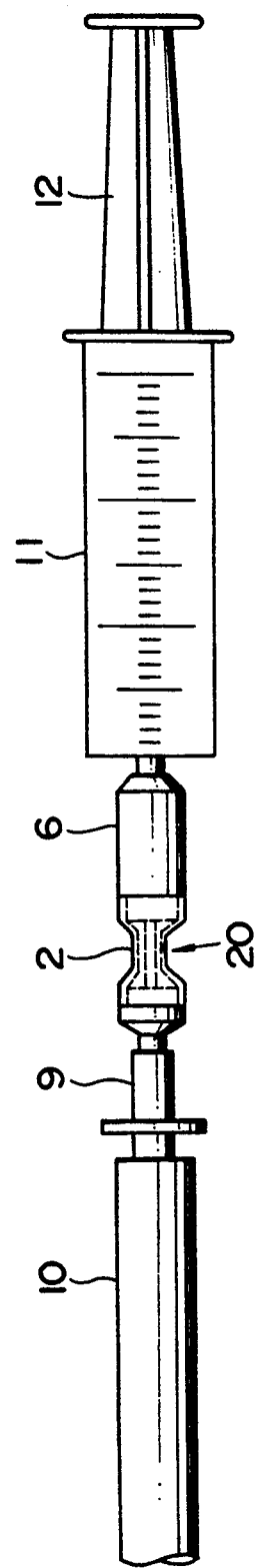
FIG. 3 is a side view illustrating a check valve and a syringe connected thereto with its piston drawn in an embodiment of an intra-aortic balloon pump apparatus according to the present invention.

Accordingly, when the piston 12 of the syringe 11 is drawn rightward in FIG. 2 to make the inside of the balloon 14 at a negative pressure, the negative pressure indicating membrane 2 is depressed as shown in FIG. 3. Since the valve member 5 shuts off the through hole 4d in the check valve 20 according to the present embodiment as described above, the chamber 7 and the space communicated therewith is maintained at the negative pressure even though the syringe 11 is pulled out from the syringe receiving member 6. Thus, it can be known that the inside of the balloon 14 is maintained at the negative pressure, as long as the negative pressure indicating membrane 2 is depressed.

Figure 6:
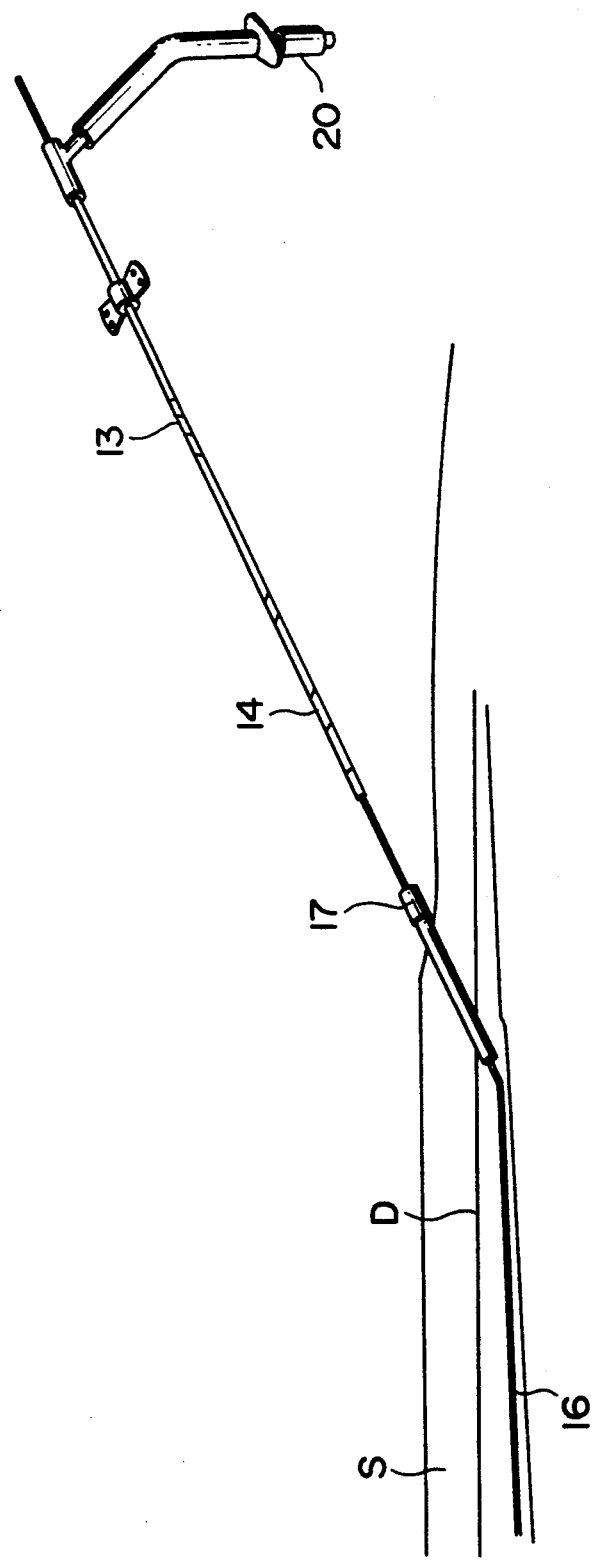
FIG. 6 is a schematic side view of an intra-aortic balloon pump apparatus with its sheath inserted into the patient according to an embodiment of the present invention.

When in use of the intra-aortic balloon pump apparatus according to the present embodiment, the cylindrical holder 15 for enclosing the balloon 14 is removed from the catheter 13 as shown in FIG. 5. At this time, the inside of the balloon 14 has been maintained at the negative pressure, so that the balloon 14 is not inflated. Then, referring to FIG. 6, a guide wire 16 is inserted into the aorta D of the patient's body S, and a sheath 17 is inserted thereinto. The catheter 13 and the balloon 14, with the guide wire 16 passing therethrough drawn out from the base portion (not shown) of the catheter 13, are inserted into the aorta D through the sheath 17 while being guided along the guide wire 16. Then, the balloon 14 is advanced to reach a predetermined position of the aorta D, so that the preparation for balloon pumping is completed.

It should be apparent to one skilled in the art that the above-described embodiments are merely illustrative of but a few of the many possible specific embodiments of the present invention. Numerous and various other arrangements can be readily devised by those skilled in the art without departing from the spirit and scope of the invention as defined in the following claims.

What is claimed is:

1. An intra-aortic balloon pump apparatus comprising:
   a catheter;
   a balloon connected to said catheter;
   a negative pressure source for withdrawing a fluid from said catheter and applying a negative pressure to said balloon through said catheter; and
   check valve means disposed between said catheter and said negative pressure source for allowing the fluid flow therethrough from said catheter to said negative pressure source and preventing the fluid from flowing from said negative pressure source to said catheter, said check valve means defining therein a pressure chamber communicated with said catheter, said check valve means being deformed when the negative pressure is applied to said pressure chamber.

2. An intra-aortic balloon pump apparatus according to claim 1, said negative pressure source comprises a syringe detachably connected to said check valve means for withdrawing the fluid from said catheter through said pressure chamber.

3. An intra-aortic balloon pump apparatus according to claim 1, wherein said check valve means comprises:
   a connecting member having a first passage defined therethrough;
   a valve base having a second passage defined therethrough and a recess formed on one end surface thereof and communicated with said second passage to provide a valve seat;
   a valve member received in said recess and seated on said valve seat for allowing the fluid flow therethrough from said catheter to said negative pressure source and preventing the fluid from flowing from said negative pressure source to said catheter;
   a bridge member disposed between one end surface of said connecting member and the other end surface of said valve base for supporting said connecting member in spaced relationship with said valve base; and
   a membrane tube disposed between said connecting member and said valve base for defining therein said pressure chamber and enclosing therein said bridge member, said pressure chamber being communicated with said first and second passages, and said membrane tube being depressed inwardly when the negative pressure is applied to said pressure chamber.

4. An intra-aortic balloon pump apparatus according to claim 2, wherein said bridge member has flange portions at its both ends with holes defined axially therethrough to communicate said first and second passages with said pressure chamber.

5. An intra-aortic balloon pump apparatus according to claim 2, wherein said check valve means further comprises a receiving member having a third passage defined therethrough and connected to said valve base for communicating said recess with said negative pressure source.

6. An intra-aortic balloon pump apparatus according to claim 4, wherein said negative pressure source comprises a syringe with a tip end thereof fitted into said third passage of said receiving member for withdrawing the fluid from said catheter through said pressure chamber.

* * * * *